United States Patent [19]

Travis et al.

[11] 4,070,153
[45] Jan. 24, 1978

[54] PREPARATION OF SERUM STANDARD FOR RADIOASSAY OF THYROXINE

[75] Inventors: Karen L. Travis, Corning; Frank B. Ward, Painted Post, both of N.Y.

[73] Assignee: Corning Glass Works, Corning, N.Y.

[21] Appl. No.: 697,401

[22] Filed: June 18, 1976

Related U.S. Application Data

[63] Continuation-in-part of Ser. No. 564,068, March 28, 1975, abandoned.

[51] Int. Cl.$^2$ ............................................. G01N 33/16
[52] U.S. Cl. ................................. 23/230.6; 23/230 B; 23/230.3; 424/1
[58] Field of Search ................. 23/230 B, 230.3, 230.6

[56] References Cited

U.S. PATENT DOCUMENTS

| | | | |
|---|---|---|---|
| 3,666,854 | 5/1972 | Eisentraut | 23/230.6 X |
| 3,743,482 | 7/1973 | Eisentraut | 23/230.6 X |
| 3,775,615 | 11/1973 | Eisentraut | 23/230.6 X |
| 3,947,564 | 3/1976 | Shannon | 23/230 B |
| 3,962,039 | 6/1976 | Bates | 23/230 B |
| 3,970,746 | 7/1976 | Premachandra | 23/230 B |
| 4,005,187 | 1/1977 | Kilthau | 23/230 B |

OTHER PUBLICATIONS

Ingbar et al., Endocrinology, vol. 61, pp. 321–326, (1957).

*Primary Examiner*—Sidney Marantz
*Attorney, Agent, or Firm*—James A. Giblin; Clinton S. Janes, Jr.; Clarence R. Patty, Jr.

[57] ABSTRACT

Thyroxine binding globulin (TBG) and thyroxine ($T_4$) can be efficiently removed from serum containing TBG and $T_4$ by contacting the serum with finely-divided alumina particles to adsorb a major portion of the $T_4$ and then reacting the serum at an acidic pH with an anion exchange resin to extract substantially all TBG and the remaining $T_4$.

7 Claims, No Drawings

PREPARATION OF SERUM STANDARD FOR RADIOASSAY OF THYROXINE

RELATED APPLICATION

This application is a continuation-in-part of our pending application Ser. No. 564,068, filed Mar. 28, 1975, now abandoned.

BACKGROUND OF THE INVENTION

1. Field

This invention is concerned generally with the preparation of serum standards useful for radioassays and specifically with the preparation of a serum standard useful for the radioimmunoassay of $T_4$.

2. Prior Art

Radioassays of $T_4$ in human serum commonly require a human serum based standard substantially free of $T_4$. Although free $T_4$ can be removed from human serum by known means (e.g., repetitive exposure to anion exchange resins), it is known that such serum commonly also contains TBG which has a relatively high binding affinity for $T_4$. When $T_4$ is bound to TBG, it is difficult to extract by conventional means since it is not free. The removal or inactivation of TBG facilitates $T_4$ removal but conventional methods have various known disadvantages. For example, various blocking agents can be used to prevent $T_4$ from binding to TBG, thereby facilitating $T_4$ extraction or precluding TBG interference in $T_4$ assays. Other methods of preparing a serum standard substantially free of $T_4$ include the use of a charcoal absorbant which is relatively messy and time consuming or the use of anion exchange resin which, though relatively cleaner, requires a minimum of four days contact with the serum. Although it is known that certain crystalline inorganics can be used to preferentially adsorb $T_4$ from serum (e.g. U.S. Pat. Nos. 3,666,854; 3,743,482; and 3,775,615 to Eisentraut) and that thyroxine can be extracted with an acidic ion exchange resin (e.g. Ingbar et al., Endocrinology, V. 61, pp. 321-326, 1957), we have found that by combining those general techniques under limited conditions, substantially all $T_4$ and TBG can be removed from serum in a quick, simple, two step reaction which, surprisingly, takes less than eight hours.

SUMMARY OF THE INVENTION

The $T_4$ serum standard is prepared by contacting a human serum containing TBG and $T_4$ with finely-divided alumina particles to adsorb a major portion (at least about 50%) of the $T_4$, and then reacting the serum under acidic conditions with an anion exchange resin for a period of time sufficient to extract substantially all TBG and remaining $T_4$. The entire process can be performed in less than eight hours. In a preferred embodiment, the serum (or plasma) is contacted with 30-45 mesh alumina particles, the amount being sufficient to adsorb a major portion ($\geq 50\%$) of the $T_4$, preferably at least about 10% by weight alumina to serum, and the subsequent reaction with the resin is at a pH of about 4.0. In such an embodiment, both reactions are completed in about 6 hours.

EXAMPLE I

Ten grams of alumina particles of 30-45 mesh, United States Standard Sieve, are incubated with 100 ml. of defibrinated human plasma in a shaking bath at 23° C. for 2 hours. The alumina is then removed by centrifugation and the pH of the decanted plasma is adjusted to about 4.0 with 1.0N HCl. Thirty grams of an analytical grade anion exchange resin (Biorad, A6-1-X10) are added to the plasma and the mixture is incubated in a shaker bath at 23° C. for 4 hours. The resin is then removed by centrifugation. The procedure is completed in considerably less time than past processes, is relatively clean, and results in the removal of substantially all TBG and $T_4$.

EXAMPLE II

In a subsequent control experiment, a parallel set of reactions was designed to investigate the possible mechanism whereby substantially all $T_4$ was extracted from the serum. In one sequence, a 10 ml sample of normal serum was reacted with the alumina and then the resin. $T_4$ and TBG concentrations were measured after each step. In another sequence, the same measurements were made, but the reaction with the alumina was eliminated. Except for the presence or absence of the alumina, all other conditions were identical. The results are summarized in the Table.

TABLE

| Reaction or Assay Step | Present Method | Control |
|---|---|---|
| 1. Initial TBG in 10 ml normal serum (μg/ml) | 17 | 17 |
| 2. Initial $T_4$ (ng/ml) | 86 | 86 |
| 3. Reaction with alumina, 1g, 30-45 mesh, for 2 hours | Yes | No |
| 4. TBG after Step 3 (μg/ml) | 15.3 | 17 |
| 5. $T_4$ after Step 3 (ng/ml) | 43 | 86 |
| 6. Reaction with anion exchange resin, 3g, for 4 hrs., pH 4.0 | Yes | Yes |
| 7. Final TBG (μg/ml) | 0.3 | 14 |
| 8. Final $T_4$ (ng/ml) | 4 | 50 |

The above results clearly indicate the unexpected advantages of reacting the serum with the alumina prior to resin extraction to obtain a substantially $T_4$ free serum standard.

We claim:

1. A method of preparing a serum standard useful for radioassays of thyroxine, the method comprising: contacting a human serum containing thyroxine binding globulin and thyroxine with finely-divided alumina particles to remove a major portion of the thyroxine, and then reacting the serum at an acidic pH with an anion exchange resin for a period of time sufficient to extract substantially all thyroxine binding globulin and the remaining thyroxine.

2. The method of claim 1 wherein the weight of the alumina is at least about 10% of the serum weight.

3. The method of claim 1 wherein the reaction with the resin is at a pH of about 4.0.

4. A method of claim 1 wherein the alumina particles have a particle size of about 30-45 mesh.

5. The method of claim 1 wherein the weight of the alumina particles is at least about 10% of the serum weight, the particles have a particle size of 30-45 mesh, and the reaction with the resin is at a pH of about 4.0.

6. The method of claim 5 wherein the total reaction time of both steps is less than 8 hours.

7. The method of claim 6 wherein the total reaction time is about 6 hours.

* * * * *